US007393259B2

(12) United States Patent
Heo et al.

(10) Patent No.: US 7,393,259 B2
(45) Date of Patent: Jul. 1, 2008

(54) METHOD OF FORMING EMITTERS AND METHOD OF MANUFACTURING FIELD EMISSION DEVICE (FED)

(75) Inventors: Jeong-Na Heo, Yongin-si (KR); Shang-Hyeun Park, Boryeong-si (KR); Tae-Won Jeong, Seoul (KR)

(73) Assignee: Samsung SDI Co., Ltd., Suwon-si, Gyeonggi-do (KR)

( * ) Notice: Subject to any disclaimer, the term of this patent is extended or adjusted under 35 U.S.C. 154(b) by 522 days.

(21) Appl. No.: 11/199,247

(22) Filed: Aug. 9, 2005

(65) Prior Publication Data

US 2006/0035561 A1 Feb. 16, 2006

(30) Foreign Application Priority Data

Aug. 10, 2004 (KR) ...................... 10-2004-0062774

(51) Int. Cl.
*H01J 9/00* (2006.01)
*B82B 3/00* (2006.01)
*A61K 9/14* (2006.01)

(52) U.S. Cl. ............................ 445/50; 264/29.1; 264/5; 423/445 B; 424/489

(58) Field of Classification Search ............. 445/49-51; 424/489; 264/5, 81, 319, 29.1
See application file for complete search history.

(56) References Cited

U.S. PATENT DOCUMENTS 6,866,801 B1 * 3/2005 Mau et al. .................. 264/29.1
2004/0191321 A1 * 9/2004 Guan et al. ................. 424/489

FOREIGN PATENT DOCUMENTS

JP 2006054185 A * 2/2006

* cited by examiner

*Primary Examiner*—Joseph L Williams
(74) *Attorney, Agent, or Firm*—Robert E. Bushnell, Esq.

(57) ABSTRACT

A method of forming emitters and a method of manufacturing a Field Emission Device (FED) using the method includes: forming a volume-changeable structure on an electrode, the volume-changeable structure composed of a polymer which reversibly swells and shrinks in response to an external stimulus; injecting an electron-emitting material into the volume-changeable structure; aligning the electron-emitting material; and removing the polymer to form the emitters.

50 Claims, 9 Drawing Sheets

METHOD OF FORMING EMITTERS AND METHOD OF MANUFACTURING FIELD EMISSION DEVICE (FED)

CLAIM OF PRIORITY

This application makes reference to, incorporates the same herein, and claims all benefits accruing under 35 U.S.C. § 119 from an application for METHOD OF FORMING EMITTERS AND METHOD OF MANUFACTURING FIELD EMISSION DEVICE earlier filed in the Korean Intellectual Property Office on 10 Aug. 2004 and there duly assigned Ser. No. 10-2004-0062774.

BACKGROUND OF THE INVENTION

1. Field of the Invention

The present invention relates to a method of forming emitters and a method of manufacturing a Field Emission Device (FED), and more particularly, to a method of forming emitters at a low temperature that can be applied to a complicated structure and a method of manufacturing an FED.

2. Description of the Related Art

FEDs are devices that emit electrons from emitters formed on a cathode electrode by applying a strong electric field between the cathode electrode and a gate electrode. Recently, carbon nano-tube emitters which use Carbon Nano-Tubes (CNTs) as an electron-emitting material are primarily used as electron-emitters in the FEDs.

Methods of forming carbon nano-tube emitters include a method of growing CNTs directly on a substrate and a method of making CNTs from a paste.

However, in the former method, since CNTs are grown directly on the substrate, it is difficult to manufacture a large FED. In addition, the method requires a high temperature, and thus, the use of a glass substrate can cause a problem. The latter method requires an additional process of aligning CNTs, and accordingly, the CNTs can only be applied with difficultly to a complicated structure.

SUMMARY OF THE INVENTION

The present invention provides a method of forming emitters at a low temperature that can be applied to a complicated structure.

The present invention also provides a method of manufacturing a Field Emission Device (FED) using the method of forming emitters.

According to one aspect of the present invention, a method of forming emitters is provided, the method comprising: forming a volume-changeable structure on an electrode, the volume-changeable structure including a polymer which reversibly swells and shrinks in response to an external stimulus; injecting an electron-emitting material into the volume-changeable structure; aligning the electron-emitting material; and removing the polymer to form the emitters.

Forming the volume-changeable structure preferably comprises coating the polymer on a substrate and the electrode formed on the substrate and patterning the polymer.

Forming the volume-changeable structure preferably further comprises removing water from the patterned polymer.

The polymer preferably comprises an Electro-Active Polymer (EAP) or a hydrogel.

The polymer preferably comprises at least one polymer selected from the group consisting of PDMS, PMA, PAA, PNIPAAm, PAM, HA, AL, PVA, PDADMAC, SA, AAm, NIPAAm, PVME, PEG, PPG, MC, PDEAEM, glucose, chitosan, and gelatin.

Injecting the electron-emitting material into the volume-changeable structure preferably comprises repeatedly swelling and shrinking the volume-changeable structure.

Repeatedly swelling and shrinking the volume-changeable structure preferably comprises placing the volume-changeable structure in a first aqueous solution including the electron-emitting material and repeatedly applying an external stimulus to the volume-changeable structure and removing the external stimulus from the volume-changeable structure.

The external stimulus preferably comprises at least one stimulus selected from the group consisting of a temperature, a pH, an electric field, and light.

The electron-emitting material preferably comprises at least one material selected from the group consisting of Carbon Nano-Tubes (CNTs), amorphous carbon, nano-diamonds, metal nano-wires, and metal oxide nano-wires.

The first aqueous solution preferably further comprises conductive nano-particles for supporting the electron-emitting material on the electrode, the conductive nano-particles being injected into the volume-changeable structure together with the electron-emitting material.

Aligning the electron-emitting material preferably comprises swelling the volume-changeable structure.

Swelling the volume-changeable structure preferably comprises placing the volume-changeable structure in a second aqueous solution, and applying an external stimulus to the volume-changeable structure and removing the applied external stimulus from the volume-changeable structure.

The external stimulus preferably comprises at least one stimulus selected from the group consisting of a temperature, a pH, an electric field, and light.

Removing the polymer preferably comprises heating or a plasma treatment.

According to another aspect of the present invention, a method of forming emitters is provided, the method comprising: forming a volume-changeable structure on an electrode, the volume-changeable structure comprising an electron-emitting material and a polymer which reversibly swells and shrinks in response to an external stimulus; aligning the electron-emitting material; and removing the polymer to form the emitters.

Forming the volume-changeable structure preferably comprises coating the polymer on a substrate and the electrode formed on the substrate and patterning the polymer.

Forming the volume-changeable structure preferably further comprises removing water from the patterned polymer.

The electron-emitting material preferably comprises at least one material selected from the group consisting of CNTs, amorphous carbon, nano-diamonds, metal nano-wires, and metal oxide nano-wires.

The polymer preferably comprises an EAP or a hydrogel.

The polymer preferably comprises at least one polymer selected from the group consisting of PDMS, PMA, PAA, PNIPAAm, PAM, HA, AL, PVA, PDADMAC, SA, AAm, NIPAAm, PVME, PEG, PPG, MC, PDEAEM, glucose, chitosan, and gelatin.

The volume-changeable structure preferably further comprises conductive nano-particles for supporting the electron-emitting material on the electrode.

Aligning the electron-emitting material preferably comprises swelling the volume-changeable structure.

Swelling the volume-changeable structure preferably comprises placing the volume-changeable structure in an aqueous solution, and applying an external stimulus to the volume-changeable structure and removing the applied external stimulus from the volume-changeable structure.

The external stimulus preferably comprises at least one stimulus selected from the group consisting of a temperature, a pH, an electric field, and light.

Removing the polymer preferably comprises heating or a plasma treatment.

According to still another aspect of the present invention, a method of manufacturing a Field Emission Device (FED) is provided, the method comprising: forming a cathode electrode, an insulating layer, and a gate electrode sequentially on a substrate and forming an emitter aperture exposing a portion of the cathode electrode in the insulating layer; forming a volume-changeable structure in the emitter aperture, the volume-changeable structure comprising a polymer which reversibly swells and shrinks in response to an external stimulus; injecting an electron-emitting material into the volume-changeable structure; aligning the electron-emitting material; and removing the polymer to form emitters.

Forming the volume-changeable structure preferably comprises: coating a photoresist on the gate electrode and the cathode electrode and patterning the photoresist to expose a portion of the cathode electrode; coating the polymer on the photoresist and the top surface of the exposed cathode electrode; patterning the polymer with a photo-lithographic process by a back-side exposure using the photoresist as a photomask; and removing the photoresist.

Forming the volume-changeable structure further preferably comprises removing water from the patterned polymer.

The polymer preferably comprises an EAP or a hydrogel.

The polymer preferably comprises at least one polymer selected from the group consisting of PDMS, PMA, PAA, PNIPAAm, PAM, HA, AL, PVA, PDADMAC, SA, AAm, NIPAAm, PVME, PEG, PPG, MC, PDEAEM, glucose, chitosan, and gelatin.

Injecting the electron-emitting material into the volume-changeable structure preferably comprises repeatedly swelling and shrinking the volume-changeable structure.

Repeatedly swelling and shrinking the volume-changeable structure preferably comprises placing the volume-changeable structure in a first aqueous solution including the electron-emitting material and repeatedly applying the external stimulus to the volume-changeable structure and removing the external stimulus from the volume-changeable structure.

The external stimulus preferably comprises at least one stimulus selected from the group consisting of a temperature, a pH, an electric field, and light.

The electron-emitting material preferably comprises at least one electron-emitting material selected from the group consisting of CNTs, amorphous carbon, nano-diamonds, metal nano-wires, and metal oxide nano-wires.

The first aqueous solution preferably further comprises conductive nano-particles for supporting the electron-emitting material on the cathode electrode, the conductive nano-particles being injected into the volume-changeable structure together with the electron-emitting material.

Aligning the electron-emitting material preferably comprises swelling the volume-changeable structure.

Swelling the volume-changeable structure preferably comprises placing the volume-changeable structure in which the electron-emitting material has been injected in a second aqueous solution, and applying an external stimulus to the volume-changeable structure and removing the applied external stimulus from the volume-changeable structure.

The external stimulus preferably comprises at least one stimulus selected from the group consisting of a temperature, a pH, an electric field, and light.

Removing the polymer preferably comprises heating or a plasma treatment.

According to still another aspect of the present invention, a method of manufacturing a Field Emission Device (FED) is provided, the method comprising: forming a cathode electrode, an insulating layer, and a gate electrode sequentially on a substrate and forming an emitter aperture exposing a portion of the cathode electrode in the insulating layer; forming a volume-changeable structure comprising an electron-emitting material and a polymer which reversibly swells and shrinks in response to an external stimulus in the emitter aperture; aligning the electron-emitting material; and removing the polymer to form emitters.

Forming the volume-changeable structure preferably comprises: coating a photoresist on the gate electrode and the cathode electrode and patterning the photoresist to expose a portion of the cathode electrode; coating the polymer containing the electron-emitting material on the photoresist and the top surface of the exposed cathode electrode; patterning the polymer using a photolithographic process by a back-side exposure using the photoresist as a photomask; and removing the photoresist.

Forming the volume-changeable structure preferably further comprises removing water from the patterned polymer.

The electron-emitting material preferably comprises at least one material selected from the group consisting of CNTs, amorphous carbon, nano-diamonds, metal nano-wires, and metal oxide nano-wires.

The polymer preferably comprises an EAP or a hydrogel.

The polymer preferably comprises at least one polymer selected from the group consisting of PDMS, PMA, PAA, PNIPAAm, PAM, HA, AL, PVA, PDADMAC, SA, AAm, NIPAAm, PVME, PEG, PPG, MC, PDEAEM, glucose, chitosan, and gelatin.

The volume-changeable structure preferably further comprises conductive nano-particles for supporting the electron-emitting material on the cathode electrode.

Aligning the electron-emitting material preferably comprises swelling the volume-changeable structure.

Swelling the volume-changeable structure preferably comprises placing the volume-changeable structure in an aqueous solution, and applying an external stimulus to the volume-changeable structure and removing the applied external stimulus from the volume-changeable structure.

The external stimulus preferably comprises at least one stimulus selected from the group consisting of a temperature, a pH, an electric field, and light.

Removing the polymer preferably comprises heating or a plasma treatment.

BRIEF DESCRIPTION OF THE DRAWINGS

A more complete appreciation of the present invention, and many of the attendant advantages thereof, will be readily apparent as the present invention becomes better understood by reference to the following detailed description when considered in conjunction with the accompanying drawings in which like reference symbols indicate the same or similar components, wherein.

DETAILED DESCRIPTION OF THE INVENTION

Figure 1A:
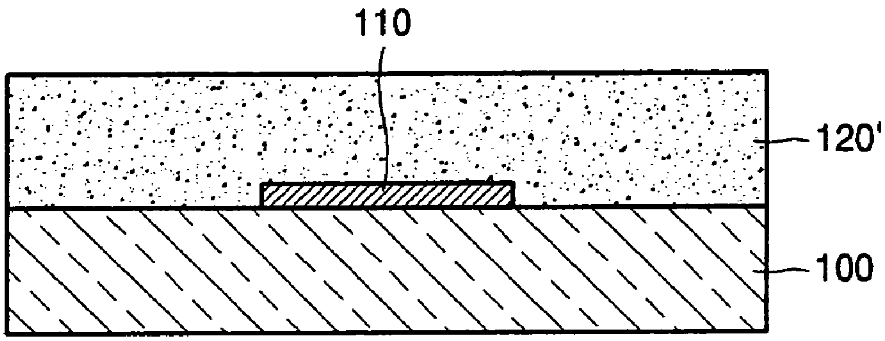
FIGS. 1A through 1F are views of a method of forming emitters according to an embodiment of the present invention.

Hereinafter, the present invention is described in more detail with reference to the following examples. Throughout the drawings, like reference numerals refer to like elements.

FIGS. 1A through 1F are views of a method of forming emitters according to an embodiment of the present invention.

Referring to FIG. 1A, a predetermined polymer 120' is coated on a substrate 100 and an electrode 110 is formed on the substrate 100. The polymer 120' is a material which reversibly swells and shrinks in response to an external stimulus, such as an Electro-Active Polymer (EAP) and a hydrogel. Specifically, the polymer 120' can be composed of at least one polymer selected from the group consisting of PDMS (poly (dimethylsiloxane)), PMA (poly(methacrylic acid)), PAA (poly(acrylic acid)), PNIPAAm (poly(N-isopropylacrylamide)), PAM (polyarylamide), HA (hyaluronic acid), AL (alginate), PVA (polyvinylalchol), PDADMAC (poly(diallyldimethylammonium chloride)), SA (sodium alginate), AAm (acrylamide), NIPAAm (N-isopropylacrylamide), PVME (poly(vinyl methyl ether)), PEG (poly(ethylene glycol)), PPG (poly(propylene glycol), MC (methylcellulose), PDEAEM (poly(N,N-ethylaminoethyl methacrylate), glucose, chitosan, and gelatin.

Figure 1B:
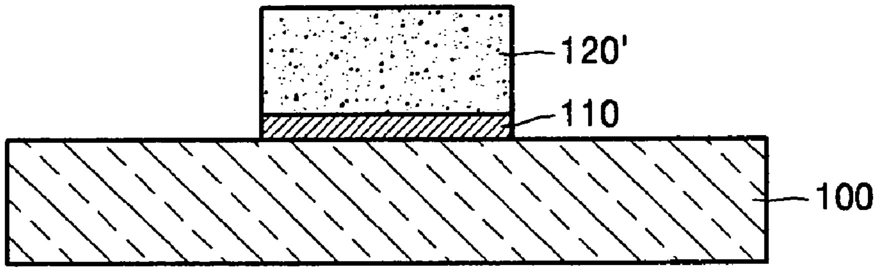
Figure 1C:
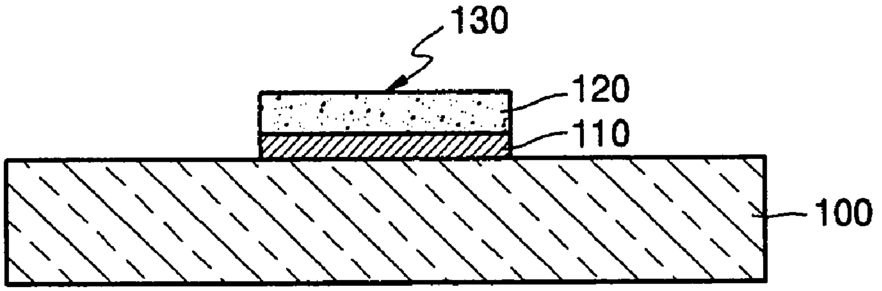

Then, as illustrated in FIG. 1B, the polymer 120' coated on the substrate 100 is patterned. Next, as illustrated in FIG. 1C, when water is removed from the patterned polymer 120', a volume-changeable structure 130 composed of a polymer 120 which reversibly swells and shrinks in response to an external stimulus is formed on the top surface of the electrode 110. Alternatively, the volume-changeable structure 130 can be composed of a polymer which is formed by electro-polymerization on the substrate 100 and the electrode 110 formed on the substrate 100.

Figure 1D:
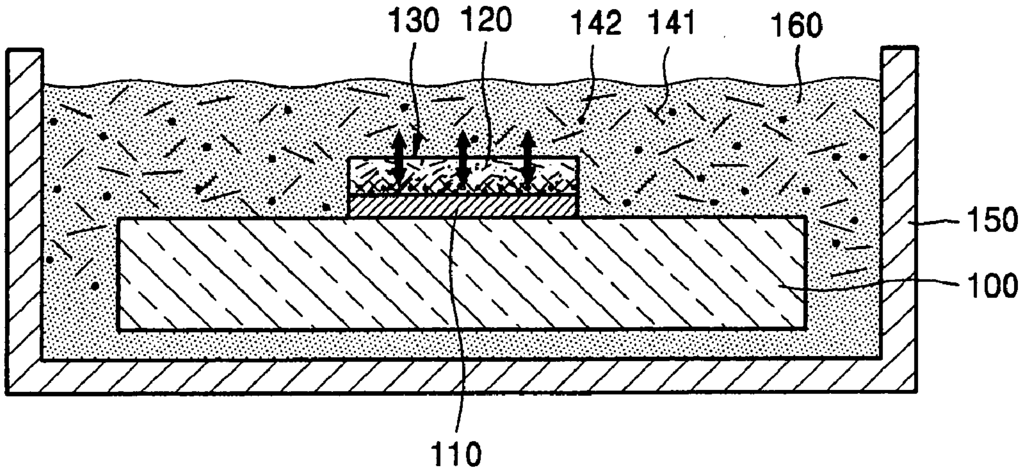

Referring to FIG. 1D, the resultant product illustrated in FIG. 1C is placed into a first aqueous solution 160 contained in a first container 150. An electron-emitting material 141 and conductive nano-particles 142 are dispersed in the first aqueous solution 160. The electron-emitting material 141 can be composed of at least one material selected from the group consisting of Carbon Nano-Tubes (CNTs), amorphous carbon, nano-diamonds, metal nano-wires, and metal oxide nano-wires. The conductive nano-particles 142 are used to support the electron-emitting material 141 on the electrode 110 and are primarily composed of nano-metal particles. When the external stimulus is repeatedly applied to and removed from the volume-changeable structure 130, with the volume-changeable structure 130 being immersed in the first aqueous solution 160, the volume-changeable structure 130 repeatedly swells and shrinks. Thus, the electron-emitting material 141 and the conductive nano-particles 142 dispersed in the first aqueous solution 160 are injected into the volume-changeable structure 130. The external stimulus can be at least one stimulus selected from the group consisting of a temperature, a pH, an electric field, and light.

Figure 1E:
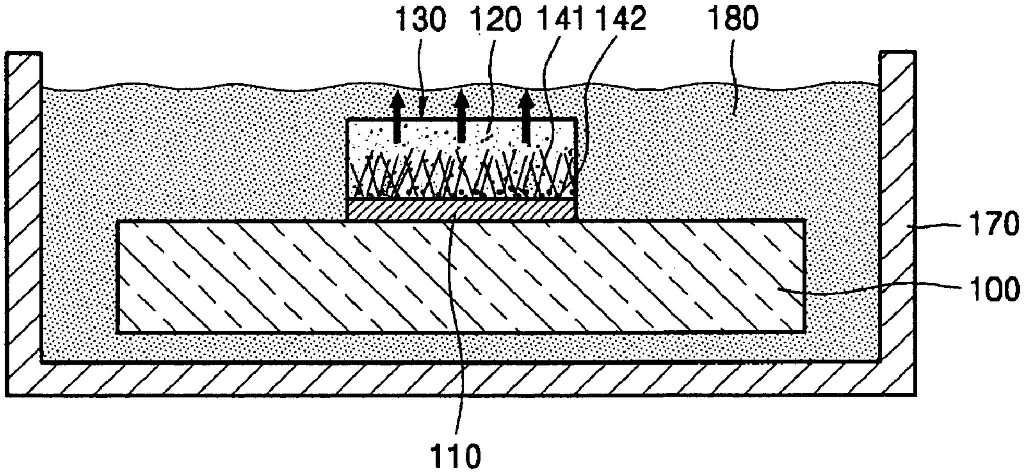

Referring to FIG. 1E, the resultant product illustrated in FIG. 1D is placed into a second aqueous solution 180 contained in a second container 170. The second aqueous solution 180 contains neither the electron-emitting material 141 nor the conductive nano-particles 142. When applying an external stimulus to the volume-changeable structure 130 or removing the applied external stimulus from the volume-changeable structure 130, with the volume-changeable structure 130 being immersed in the second aqueous solution 180, the volume-changeable structure 130 swells. Accordingly, the electron-emitting material 141 in the volume-changeable structure 130 is aligned substantially perpendicular to a surface of the electrode 110. The electron-emitting material 141 is supported on the electrode 110 by the conductive nano-particles 142. The external stimulus can be at least one stimulus selected from the group consisting of a temperature, a pH, an electric field, and light.

Figure 1F:
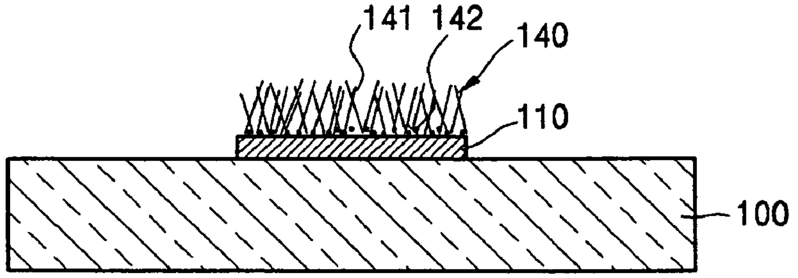

Then, when the polymer 120 is removed from the resultant product illustrated in FIG. 1E, the emitters 140 which are composed of the electron-emitting material 141 and the conductive nano-particles 142 are obtained, as illustrated in FIG. 1F. The polymer 120 can be removed by heating or a plasma treatment, for example.

FIGS. 2A through 2E are views illustrating a method of forming emitters according to another embodiment of the present invention.

Figure 2A:
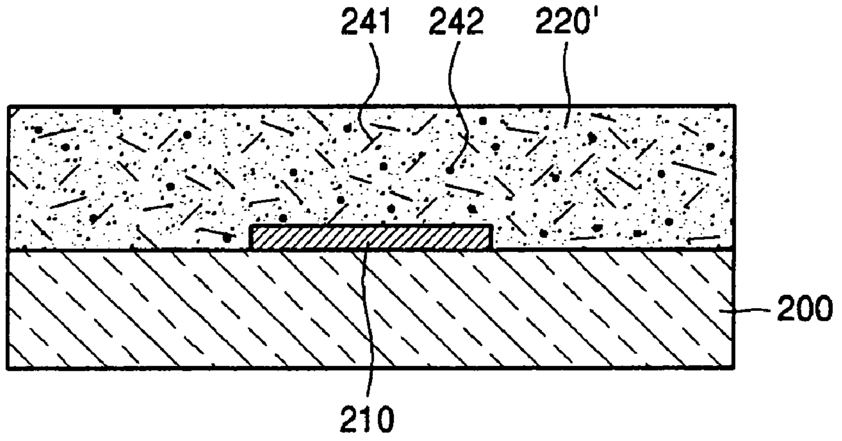
FIGS. 2A through 2E are views of a method of forming emitters according to another embodiment of the present invention.

Referring to FIG. 2A, a predetermined polymer 220' containing an electron-emitting material 241 and conductive nano-particles 242 is coated on a substrate 200 and an electrode 210 formed on the substrate 200. The electron-emitting material 241 can be composed of at least one material selected from the group consisting of CNTs, amorphous carbon, nano-diamonds, metal nano-wires, and metal oxide nano-wires. The conductive nano-particles 242 can be primarily composed of nano-metal particles. The polymer 220' is a material which reversibly swells and shrinks in response to an external stimulus, such as an EAP or a hydrogel. Specifically, the polymer 220' can be composed of at least one polymer selected from the group consisting of PDMS, PMA, PAA, PNIPAAm, PAM, HA, AL, PVA, PDADMAC, SA, AAm, NIPAAm, PVME, PEG, PPG, MC, PDEAEM, glucose, chitosan, and gelatin.

Figure 2B:
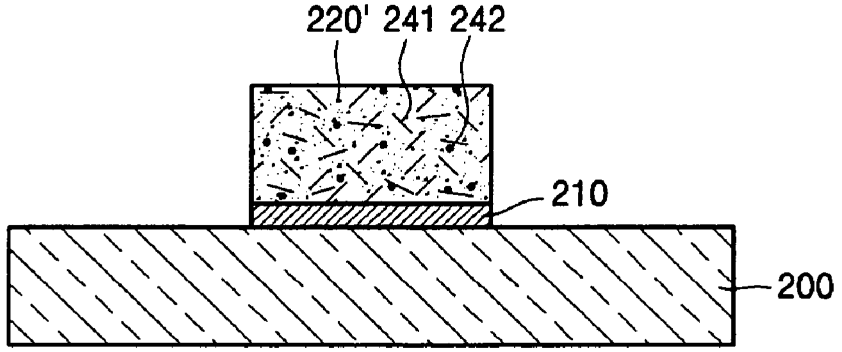
Figure 2C:
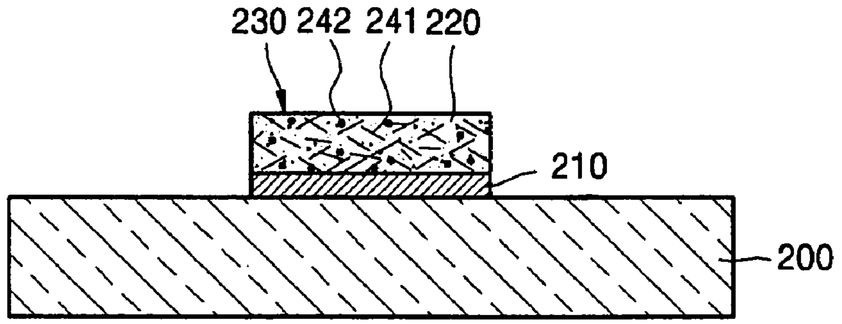

Then, as illustrated in FIG. 2B, the polymer 220' is patterned. Next, as illustrated in FIG. 2C, when water is removed from the patterned polymer 220', a volume-changeable structure 230 composed of the electron-emitting material 241, the conductive nano-particles 242, and a polymer 220 which reversibly swells and shrinks in response to an external stimulus is formed on the top surface of the electrode 210. Alternatively, the volume-changeable structure 230 can be composed of a polymer containing the electron-emitting material 241 and the conductive nano-particles 242, which is formed by electro-polymerization on the substrate 200 and the electrode 210 formed on the substrate 200.

Figure 2D:
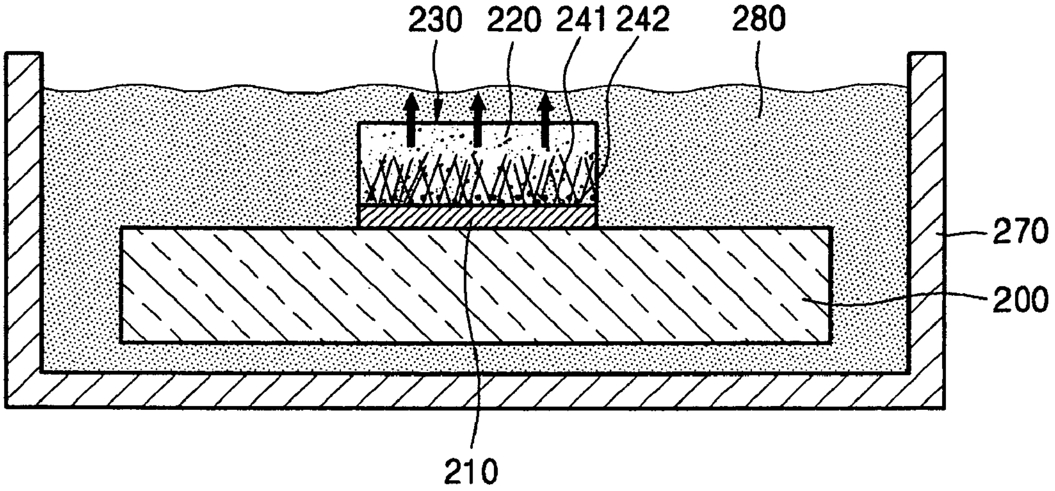

Referring to FIG. 2D, the resultant product illustrated in FIG. 2C is placed into an aqueous solution 280 contained in a container 270. The aqueous solution 280 contains neither the electron-emitting material 241 nor the conductive nano-particles 242. When applying an external stimulus to the volume-changeable structure 230 or removing the applied external stimulus from the volume-changeable structure 230, with the volume-changeable structure 230 being immersed in the aqueous solution 280, the volume-changeable structure 230 swells. Accordingly, the electron-emitting material 241 in the volume-changeable structure 230 is aligned substantially perpendicular to a surface of the electrode 210. The electron-emitting material 241 is supported on the electrode 210 by the conductive nano-particles 242. The external stimulus can be at least one stimulus selected from the group consisting of a temperature, a pH, an electric field, and light.

Figure 2E:
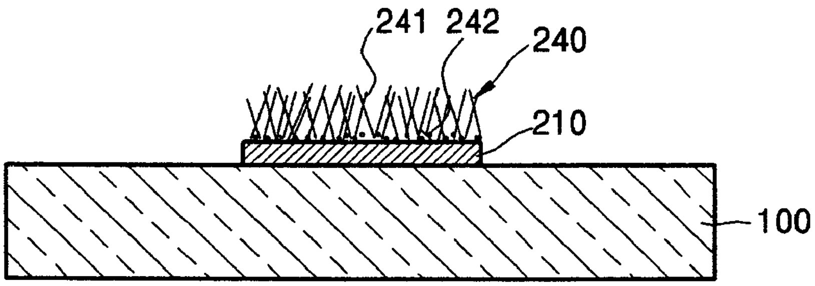

Then, when the polymer 220 is removed from the resultant product illustrated in FIG. 2D, the emitters 240 which are composed of the electron-emitting material 241 and the conductive nano-particles 242 are obtained, as illustrated in FIG. 2E. The polymer 220 can be removed by heating or plasma treatment, for example.

Hereinafter, a method of manufacturing an FED using the method of forming emitters according to embodiments of the present invention are described.

FIGS. 3A through 3G are views of a method of manufacturing an FED according to an embodiment of the present invention.

Figure 3A:
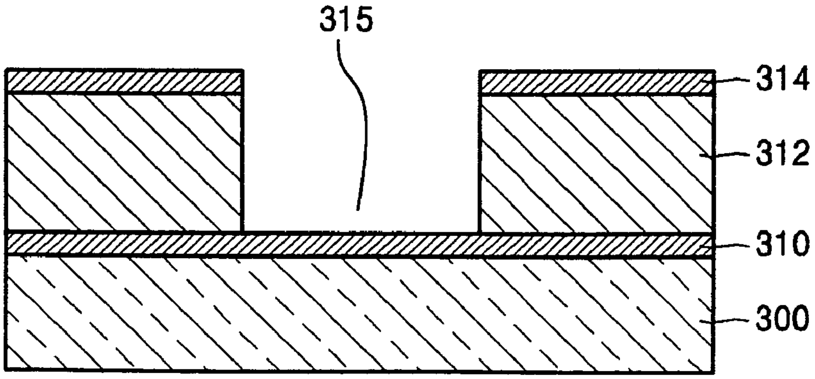
FIGS. 3A through 3G are views of a method of manufacturing a Field Emission Device (FED) according to an embodiment of the present invention.

Referring to FIG. 3A, a cathode electrode 310, an insulating layer 312, and a gate electrode 314 are sequentially formed on a substrate 300 and an emitter aperture 315 exposing a portion of the cathode electrode 310 is formed in the insulating layer 312. The substrate 300 can generally be composed of glass. The cathode electrode 310 can be composed of Indium Tin Oxide (ITO), which is a conductive transparent material. The gate electrode 314 can be composed of a conductive metal, for example, chromium (Cr).

Specifically, a cathode electrode layer which is composed of ITO is deposited on the substrate 300 to a predetermined thickness and then patterned into a predetermined pattern, for example, in the form of stripes, to obtain the cathode electrode 310. Then, the insulating layer 312 is formed on the entire surfaces of the cathode electrode 310 and the substrate 300 to a predetermined thickness. Subsequently, a gate electrode layer is formed on the insulating layer 312. The gate electrode layer is formed by depositing a conductive metal by sputtering. The gate electrode layer is patterned to a predetermined pattern to obtain the gate electrode 314. Then, an exposed portion of the insulating layer 312 through the gate electrode 314 is etched, thereby forming the emitter aperture 315 which exposes a portion of the cathode electrode 310.

Figure 3B:
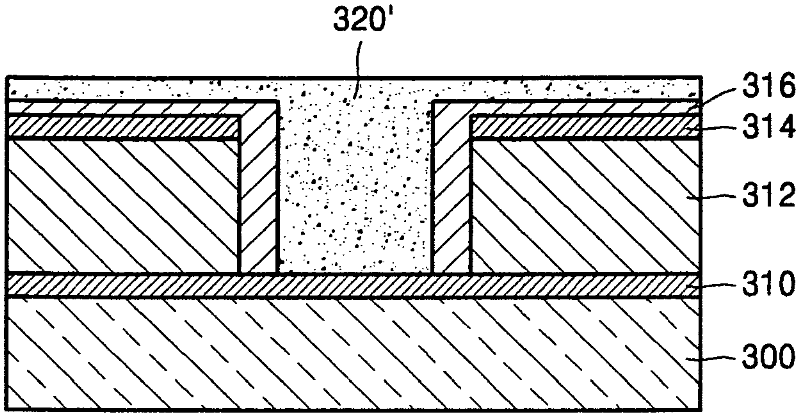

Referring to FIG. 3B, a photoresist 316 is formed on the entire surface of the resultant product illustrated in FIG. 3A to a predetermined thickness and patterned to expose a portion of the cathode electrode 310. Then, a predetermined polymer 320' is coated on the photoresist 316 and the exposed portion of the cathode electrode 310. The polymer 320' is a material which reversibly swells and shrinks in response to an external stimulus, such as an EAP or a hydrogel. Specifically, the polymer 320' can be composed of at least one polymer selected from the group consisting of PDMS, PMA, PAA, PNIPAAm, PAM, HA, AL, PVA, PDADMAC, SA, AAm, NIPAAm, PVME, PEG, PPG, MC, PDEAEM, glucose, chitosan, and gelatin.

Figure 3C:
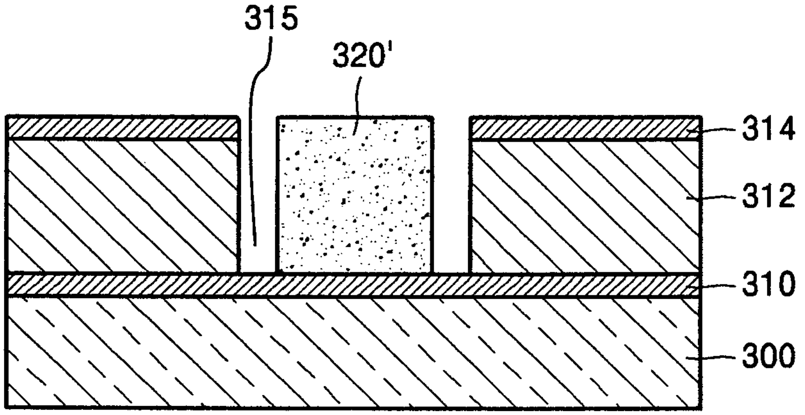
Figure 3D:
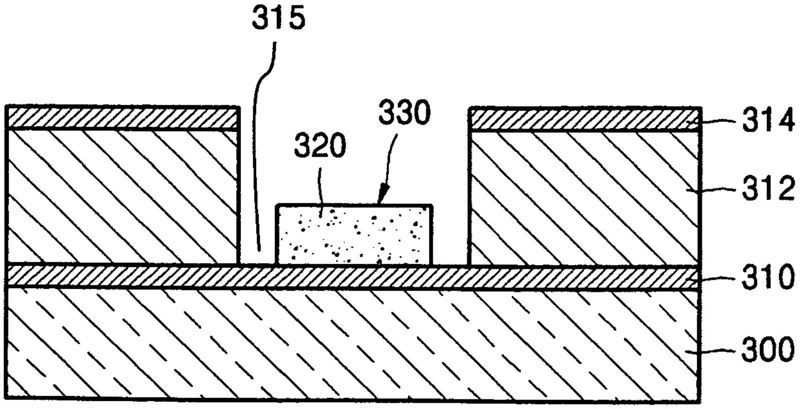

Referring to FIG. 3C, the polymer 320' is patterned using a photolithographic process by a back-side exposure in which the photoresist 316 is used as a photomask, and then, the photoresist 316 is removed. Referring to FIG. 3D, when water is removed from the polymer 320', a volume-changeable structure 330 composed of a polymer 320 which reversibly swells and shrinks in response to an external stimulus is formed in the emitter aperture 315.

Figure 3E:
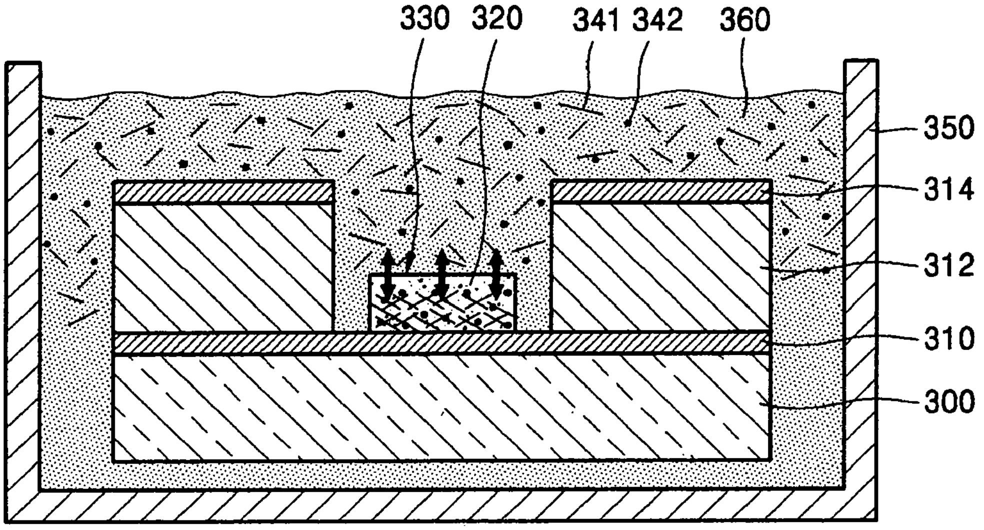

Referring to FIG. 3E, the resultant product illustrated in FIG. 3D is placed into a first aqueous solution 360 contained in a first container 350. An electron-emitting material 341 and conductive nano-particles 342 are dispersed in the first aqueous solution 360. The electron-emitting material 341 can be composed of at least one material selected from the group consisting of CNTs, amorphous carbon, nano-diamonds, metal nano-wires, and metal oxide nano-wires. The conductive nano-particles 342 are used to support the electron-emitting material 341 on the electrode 310 and are primarily composed of nano-metal particles. When the external stimulus is repeatedly applied to and removed from the volume-changeable structure 330, the volume-changeable structure 330 being immersed in the first aqueous solution 360, the volume-changeable structure 330 repeatedly swells and shrinks. Thus, the electron-emitting material 341 and the conductive nano-particles 342 dispersed in the first aqueous solution 360 are injected into the volume-changeable structure 330. The external stimulus can be at least one stimulus selected from the group consisting of a temperature, a pH, an electric field, and light.

Figure 3F:
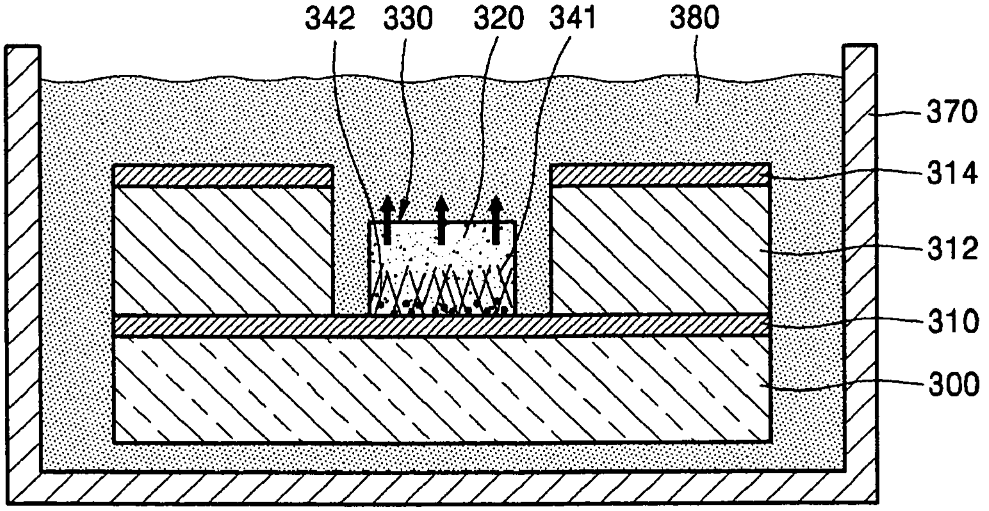

Referring to FIG. 3F, the resultant product illustrated in FIG. 3F is placed into a second aqueous solution 380 contained in a second container 370. The second aqueous solution 380 contains neither the electron-emitting material 341 nor the conductive nano-particles 342. When applying an external stimulus to the volume-changeable structure 330 or removing the applied external stimulus from the volume-changeable structure 330, with the volume-changeable structure 330 being immersed in the second aqueous solution 380, the volume-changeable structure 330 swells. Accordingly, the electron-emitting material 341 in the volume-changeable structure 330 is aligned substantially perpendicular to a surface of the electrode 310. The electron-emitting material 341 is supported on the electrode 310 by the conductive nano-particles 342. The external stimulus can be at least one stimulus selected from the group consisting of a temperature, a pH, an electric field, and light.

Figure 3G:
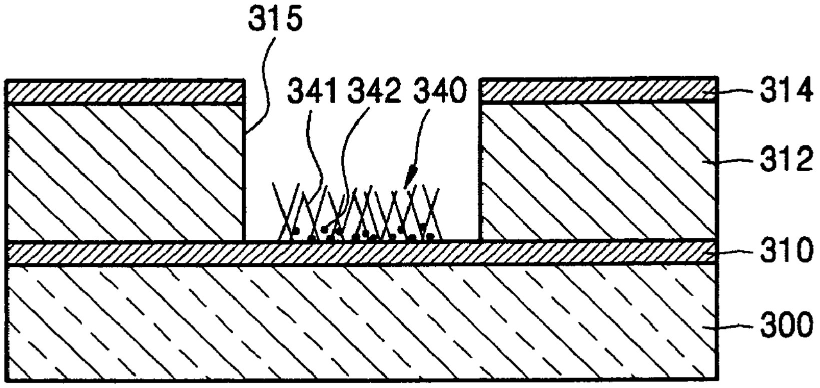

Then, when the polymer 320 is removed from resultant product illustrated in FIG. 3F, the emitters 340 which are composed of the electron-emitting material 341 and the conductive nano-particles 342 are formed in the emitter aperture 315, as illustrated in FIG. 3G. Thus, the FED is completed. The polymer 320 can be removed by heating or a plasma treatment, for example.

FIGS. 4A through 4F are views of a method of manufacturing an FED according to another embodiment of the present invention.

Figure 4A:
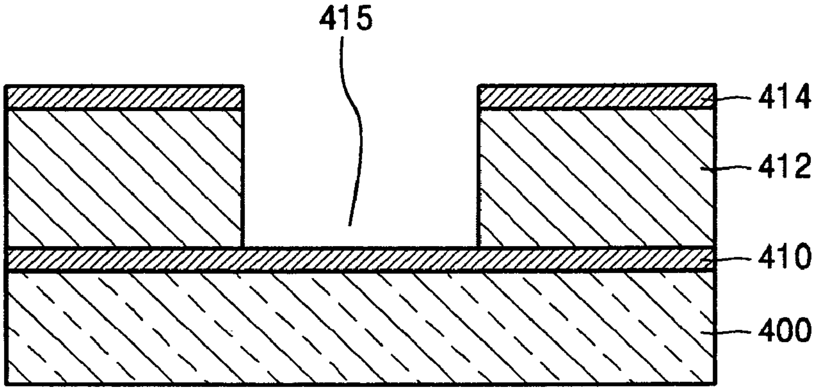
FIGS. 4A through 4F are views of a method of manufacturing an FED according to another embodiment of the present invention.

Referring to FIG. 4A, a cathode electrode 410, an insulating layer 412, and a gate electrode 414 are sequentially formed on a substrate 400 and an emitter aperture 415 exposing a portion of the cathode electrode 410 is formed in the insulating layer 412.

Figure 4B:
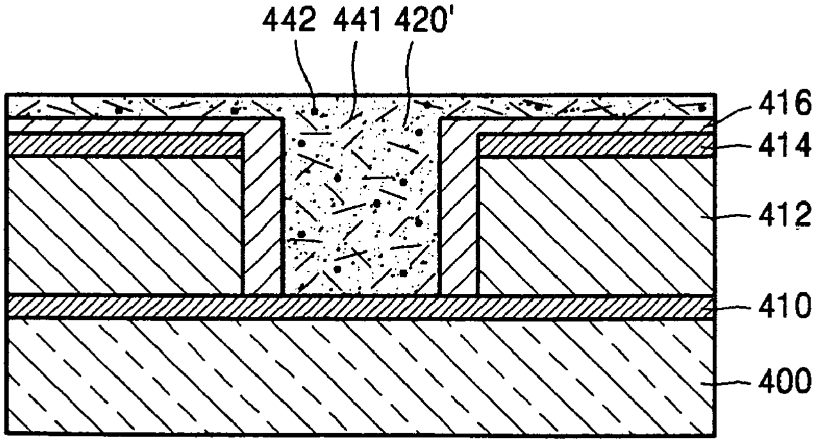

Referring to FIG. 4B, a photoresist 416 is formed on the entire surface of the resultant product illustrated in FIG. 4A to a predetermined thickness and patterned to expose a portion of the cathode electrode 410. Then, a predetermined polymer 420' comprising an electron-emitting material 441 and conductive nano-particles 442 is coated on the photoresist 416 and the exposed portion of the cathode electrode 410. The electron-emitting material 441 can be composed of at least one material selected from the group consisting of CNTs, amorphous carbon, nano-diamonds, metal nano-wires, and metal oxide nano-wires. The conductive nano-particles 442 can be primarily composed of nano-metal particles. The polymer 420' is a material which reversibly swells and shrinks in response to an external stimulus, such as an EAP or a hydrogel. Specifically, the polymer 420' can be composed of at least one polymer selected from the group consisting of PDMS, PMA, PAA, PNIPAAm, PAM, HA, AL, PVA, PDADMAC, SA, AAm, NIPAAm, PVME, PEG, PPG, MC, PDEAEM, glucose, chitosan, and gelatin.

Figure 4C:
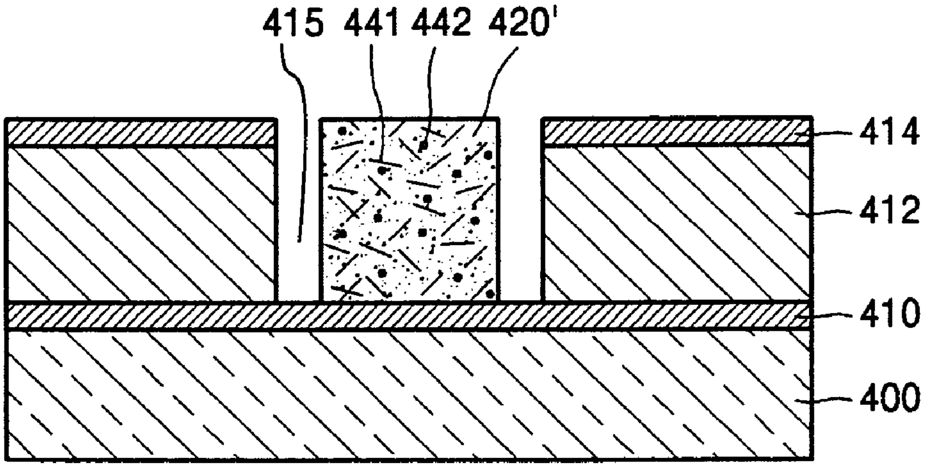
Figure 4D:
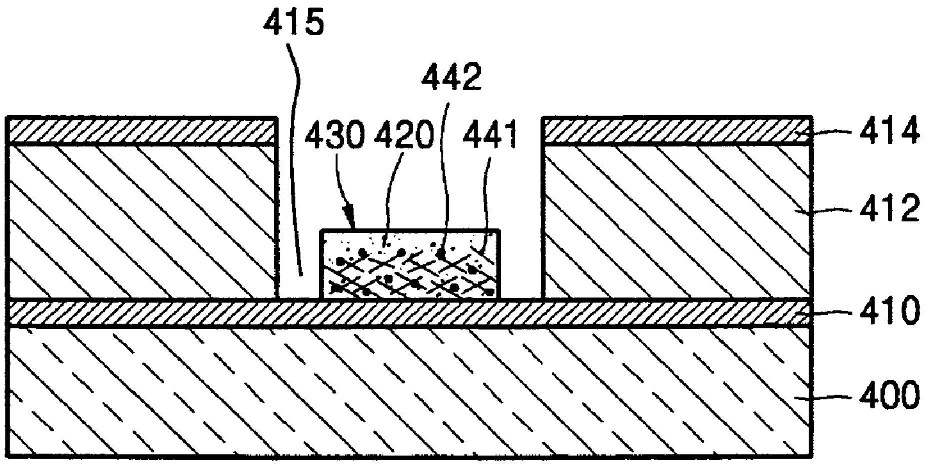

Referring to FIG. 4C, the polymer 420' is patterned using a photolithographic process by a back-side exposure in which the photoresist 416 is used as a photomask, and then, the photoresist 416 is removed. Referring to FIG. 4D, when water is removed from the polymer 420', a volume-changeable structure 430 composed of the electron-emitting material 441, the conductive nano-particles 442, and a polymer 420 which reversibly swells and shrinks in response to an external stimulus is formed in the emitter aperture 415.

Figure 4E:
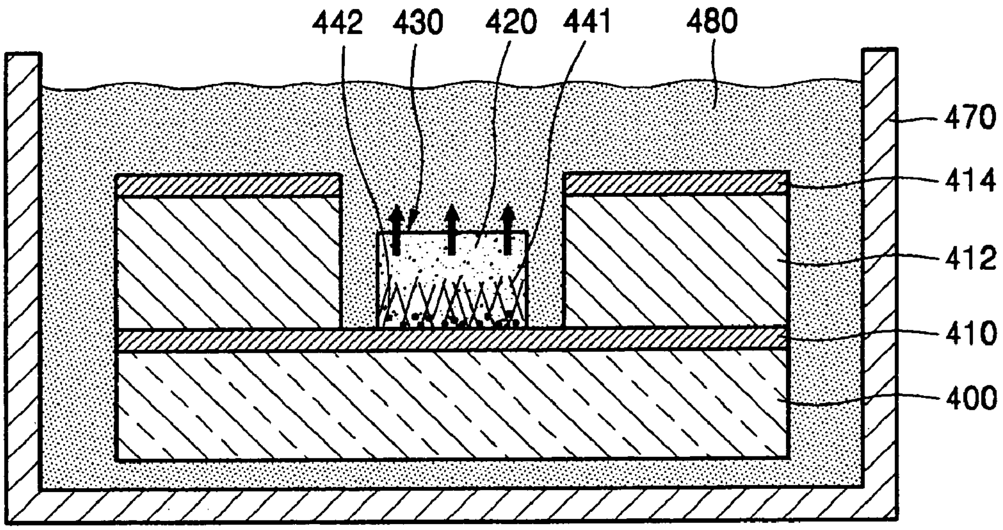

Referring to FIG. 4E, the resultant product illustrated in FIG. 4D is placed into an aqueous solution 480 contained in a container 470. The aqueous solution 480 contains neither the electron-emitting material 441 nor the conductive nano-particles 442. When applying an external stimulus to the volume-changeable structure 430 or removing the applied external stimulus from the volume-changeable structure 430, with the volume-changeable structure 430 being immersed in the aqueous solution 480, the volume-changeable structure 430 swells. Accordingly, the electron-emitting material 441 in the volume-changeable structure 430 is aligned substantially perpendicular to a surface of the electrode 410. The electron-emitting material 441 is supported on the electrode 410 by the conductive nano-particles 442. The external stimulus can be at least one stimulus selected from the group consisting of a temperature, a pH, an electric field, and light.

Figure 4F:
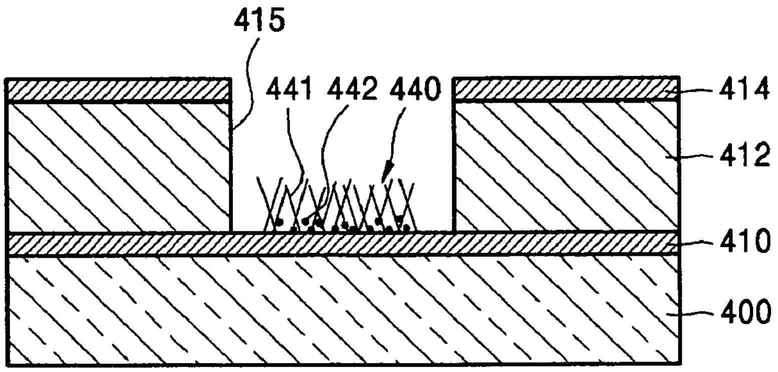

Then, when the polymer 420 is removed from the resultant product illustrated in FIG. 4E, the emitters 440 which are composed of the electron-emitting material 441 and the conductive nano-particles 442 are formed in the emitter aperture 415, as illustrated in FIG. 4F. Thus, an FED is completed. The polymer 420 can be removed by heating or a plasma treatment, for example.

As described above, by using the method of forming emitters and the method of manufacturing an FED according to the present invention, the emitters can be formed even at a low temperature and can be easily applied to a complicated structure.

While the present invention has been particularly shown and described with reference to exemplary embodiments thereof, it will be understood by those of ordinary skill in the art that various modifications in form and detail can be made therein without departing from the spirit and scope of the present invention as defined by the following claims.

What is claimed is:

1. A method of forming emitters, the method comprising:

forming a volume-changeable structure on an electrode, the volume-changeable structure including a polymer which reversibly swells and shrinks in response to an external stimulus;

injecting an electron-emitting material into the volume-changeable structure;

aligning the electron-emitting material; and removing the polymer to form the emitters.

2. The method of claim 1, wherein forming the volume-changeable structure comprises coating the polymer on a substrate and the electrode formed on the substrate and patterning the polymer.

3. The method of claim 2, wherein forming the volume-changeable structure further comprises removing water from the patterned polymer.

4. The method of claim 1, wherein the polymer comprises an Electro-Active Polymer (EAP) or a hydrogel.

5. The method of claim 4, wherein the polymer comprises at least one polymer selected from the group consisting of PDMS, PMA, PAA, PNIPAAm, PAM, HA, AL, PVA, PDADMAC, SA, AAm, NIPAAm, PVME, PEG, PPG, MC, PDEAEM, glucose, chitosan, and gelatin.

6. The method of claim 1, wherein injecting the electron-emitting material into the volume-changeable structure comprises repeatedly swelling and shrinking the volume-changeable structure.

7. The method of claim 6, wherein repeatedly swelling and shrinking the volume-changeable structure comprises placing the volume-changeable structure in a first aqueous solution including the electron-emitting material and repeatedly applying an external stimulus to the volume-changeable structure and removing the external stimulus from the volume-changeable structure.

8. The method of claim 7, wherein the external stimulus comprises at least one stimulus selected from the group consisting of a temperature, a pH, an electric field, and light.

9. The method of claim 7, wherein the electron-emitting material comprises at least one material selected from the group consisting of Carbon Nano-Tubes (CNTs), amorphous carbon, nano-diamonds, metal nano-wires, and metal oxide nano-wires.

10. The method of claim 7, wherein the first aqueous solution further comprises conductive nano-particles for supporting the electron-emitting material on the electrode, the conductive nano-particles being injected into the volume-changeable structure together with the electron-emitting material.

11. The method of claim 1, wherein aligning the electron-emitting material comprises swelling the volume-changeable structure.

12. The method of claim 11, wherein swelling the volume-changeable structure comprises placing the volume-changeable structure in a second aqueous solution, and applying an external stimulus to the volume-changeable structure and removing the applied external stimulus from the volume-changeable structure.

13. The method of claim 12, wherein the external stimulus comprises at least one stimulus selected from the group consisting of a temperature, a pH, an electric field, and light.

14. The method of claim 1, wherein removing the polymer comprises heating or a plasma treatment.

15. A method of forming emitters, the method comprising:

forming a volume-changeable structure on an electrode, the volume-changeable structure comprising an electron-emitting material and a polymer which reversibly swells and shrinks in response to an external stimulus;

aligning the electron-emitting material; and removing the polymer to form the emitters.

16. The method of claim 15, wherein forming the volume-changeable structure comprises coating the polymer on a substrate and the electrode formed on the substrate and patterning the polymer.

17. The method of claim 16, wherein forming the volume-changeable structure further comprises removing water from the patterned polymer.

18. The method of claim 15, wherein the electron-emitting material comprises at least one material selected from the group consisting of Carbon Nano-Tubes (CNTs), amorphous carbon, nano-diamonds, metal nano-wires, and metal oxide nano-wires.

19. The method of claim 15, wherein the polymer comprises an Electro-Active Polymer (EAP) or a hydrogel.

20. The method of claim 19, wherein the polymer comprises at least one polymer selected from the group consisting of PDMS, PMA, PAA, PNIPAAm, PAM, HA, AL, PVA, PDADMAC, SA, AAm, NIPAAm, PVME, PEG, PPG, MC, PDEAEM, glucose, chitosan, and gelatin.

21. The method of claim 15, wherein the volume-changeable structure further comprises conductive nano-particles for supporting the electron-emitting material on the electrode.

22. The method of claim 15, wherein aligning the electron-emitting material comprises swelling the volume-changeable structure.

23. The method of claim 22, wherein swelling the volume-changeable structure comprises placing the volume-changeable structure in an aqueous solution, and applying an external stimulus to the volume-changeable structure and removing the applied external stimulus from the volume-changeable structure.

24. The method of claim 23, wherein the external stimulus comprises at least one stimulus selected from the group consisting of a temperature, a pH, an electric field, and light.

25. The method of claim 15, wherein removing the polymer comprises heating or a plasma treatment.

26. A method of manufacturing a Field Emission Device (FED), the method comprising:

forming a cathode electrode, an insulating layer, and a gate electrode sequentially on a substrate and forming an emitter aperture exposing a portion of the cathode electrode in the insulating layer;

forming a volume-changeable structure in the emitter aperture, the volume-changeable structure comprising a polymer which reversibly swells and shrinks in response to an external stimulus;

injecting an electron-emitting material into the volume-changeable structure;

aligning the electron-emitting material; and removing the polymer to form emitters.

27. The method of claim 26, wherein forming the volume-changeable structure comprises:

coating a photoresist on the gate electrode and the cathode electrode and patterning the photoresist to expose a portion of the cathode electrode;

coating the polymer on the photoresist and the top surface of the exposed cathode electrode;

patterning the polymer with a photo-lithographic process by a back-side exposure using the photoresist as a photomask; and removing the photoresist.

28. The method of claim 27, wherein forming the volume-changeable structure further comprises removing water from the patterned polymer.

29. The method of claim 26, wherein the polymer comprises an Electro-Active Polymer (EAP) or a hydrogel.

30. The method of claim 29, wherein the polymer comprises at least one polymer selected from the group consisting of PDMS, PMA, PAA, PNIPAAm, PAM, HA, AL, PVA, PDADMAC, SA, AAm, NIPAAm, PVME, PEG, PPG, MC, PDEAEM, glucose, chitosan, and gelatin.

31. The method of claim 26, wherein injecting the electron-emitting material into the volume-changeable structure comprises repeatedly swelling and shrinking the volume-changeable structure.

32. The method of claim 31, wherein repeatedly swelling and shrinking the volume-changeable structure comprises placing the volume-changeable structure in a first aqueous solution including the electron-emitting material and repeatedly applying the external stimulus to the volume-changeable structure and removing the external stimulus from the volume-changeable structure.

33. The method of claim 32, wherein the external stimulus comprises at least one stimulus selected from the group consisting of a temperature, a pH, an electric field, and light.

34. The method of claim 32, wherein the electron-emitting material comprises at least one electron-emitting material selected from the group consisting of Carbon Nano-Tubes (CNTs), amorphous carbon, nano-diamonds, metal nano-wires, and metal oxide nano-wires.

35. The method of claim 32, wherein the first aqueous solution further comprises conductive nano-particles for supporting the electron-emitting material on the cathode electrode, the conductive nano-particles being injected into the volume-changeable structure together with the electron-emitting material.

36. The method of claim 26, wherein aligning the electron-emitting material comprises swelling the volume-changeable structure.

37. The method of claim 36, wherein swelling the volume-changeable structure comprises placing the volume-changeable structure in which the electron-emitting material has been injected in a second aqueous solution, and applying an external stimulus to the volume-changeable structure and removing the applied external stimulus from the volume-changeable structure.

38. The method of claim 37, wherein the external stimulus comprises at least one stimulus selected from the group consisting of a temperature, a pH, an electric field, and light.

39. The method of claim 26, wherein removing the polymer comprises heating or a plasma treatment.

40. A method of manufacturing a Field Emission Device (FED), the method comprising:

forming a cathode electrode, an insulating layer, and a gate electrode sequentially on a substrate and forming an emitter aperture exposing a portion of the cathode electrode in the insulating layer;

forming a volume-changeable structure comprising an electron-emitting material and a polymer which reversibly swells and shrinks in response to an external stimulus in the emitter aperture;

aligning the electron-emitting material; and removing the polymer to form emitters.

41. The method of claim 40, wherein forming the volume-changeable structure comprises:

coating a photoresist on the gate electrode and the cathode electrode and patterning the photoresist to expose a portion of the cathode electrode;

coating the polymer containing the electron-emitting material on the photoresist and the top surface of the exposed cathode electrode;

patterning the polymer using a photolithographic process by a back-side exposure using the photoresist as a photomask; and removing the photoresist.

42. The method of claim 41, wherein forming the volume-changeable structure further comprises removing water from the patterned polymer.

43. The method of claim 40, wherein the electron-emitting material comprises at least one material selected from the group consisting of Carbon Nano-Tubes (CNTs), amorphous carbon, nano-diamonds, metal nano-wires, and metal oxide nano-wires.

44. The method of claim 40, wherein the polymer comprises an Electro-Active Polymer (EAP) or a hydrogel.

45. The method of claim 44, wherein the polymer comprises at least one polymer selected from the group consisting of PDMS, PMA, PAA, PNIPAAm, PAM, HA, AL, PVA, PDADMAC, SA, AAm, NIPAAm, PVME, PEG, PPG, MC, PDEAEM, glucose, chitosan, and gelatin.

46. The method of claim 40, wherein the volume-changeable structure further comprises conductive nano-particles for supporting the electron-emitting material on the cathode electrode.

47. The method of claim 40, wherein aligning the electron-emitting material comprises swelling the volume-changeable structure.

48. The method of claim 47, wherein swelling the volume-changeable structure comprises placing the volume-changeable structure in an aqueous solution, and applying an external stimulus to the volume-changeable structure and removing the applied external stimulus from the volume-changeable structure.

49. The method of claim 48, wherein the external stimulus comprises at least one stimulus selected from the group consisting of a temperature, a pH, an electric field, and light.

50. The method of claim 40, wherein removing the polymer comprises heating or a plasma treatment.

* * * * *